United States Patent [19]

Tanaka et al.

[11] Patent Number: 4,966,809
[45] Date of Patent: Oct. 30, 1990

[54] WATER-ABSORBING COMPOSITE BODY

[75] Inventors: Toyoaki Tanaka, Yokohama; Katuzi Ohira, Sagamihara; Akira Nakamura, Chigasaki; Ryosuke Kamei; Akihiro Hashimoto, both of Yokohama, all of Japan

[73] Assignee: Showa Denko Kabushiki Kaisha, Tokyo, Japan

[21] Appl. No.: 155,935

[22] PCT Filed: Apr. 2, 1987

[86] PCT No.: PCT/JP87/00208
§ 371 Date: Dec. 2, 1987
§ 102(e) Date: Dec. 2, 1987

[87] PCT Pub. No.: WO87/05860
PCT Pub. Date: Oct. 8, 1987

[30] Foreign Application Priority Data

| Apr. 2, 1986 [JP] | Japan | 61-74366 |
| Apr. 7, 1986 [JP] | Japan | 61-79847 |
| Jul. 30, 1986 [JP] | Japan | 61-179221 |
| Jul. 30, 1986 [JP] | Japan | 61-179222 |
| Jul. 30, 1986 [JP] | Japan | 61-179223 |
| Jul. 30, 1986 [JP] | Japan | 61-179224 |

[51] Int. Cl.$^5$ ............... B32B 27/14; B32B 5/16; B29D 9/00
[52] U.S. Cl. ............... 428/323; 428/372; 428/374; 428/375; 428/377; 428/394; 428/395; 428/400; 428/401; 428/913; 156/271
[58] Field of Search ............... 428/375, 323, 372, 374, 428/377, 395, 394, 400, 401, 913

[56] References Cited

U.S. PATENT DOCUMENTS

| 3,935,099 | 1/1976 | Weaver et al. | 525/54.32 |
| 4,457,974 | 7/1984 | Summers | 428/374 X |
| 4,560,385 | 12/1985 | Baravian | 428/374 X |
| 4,764,427 | 8/1988 | Hara et al. | 428/374 X |

Primary Examiner—P. C. Ives

[57] ABSTRACT

Disclosed is a water-absorbing composite body comprising a tape-shaped laminate having at least one layer of a high-melting-point synthetic resin and at least one layer of a low-melting-point synthetic resin, in which at least a part of the low-melting-point synthetic resin layer is exposed to the surface, a split fiber obtained by splitting this tape-shaped laminate or a composite fibrous body having a laminate structure as described above, and a powdery polymeric water absorber fusion-bonded to the outer surface of the low-melting-point synthetic resin layer exposed to the surface. This water-absorbing composite body has a high water-absorbing capacity and retains a good mechanical strength.

15 Claims, 2 Drawing Sheets

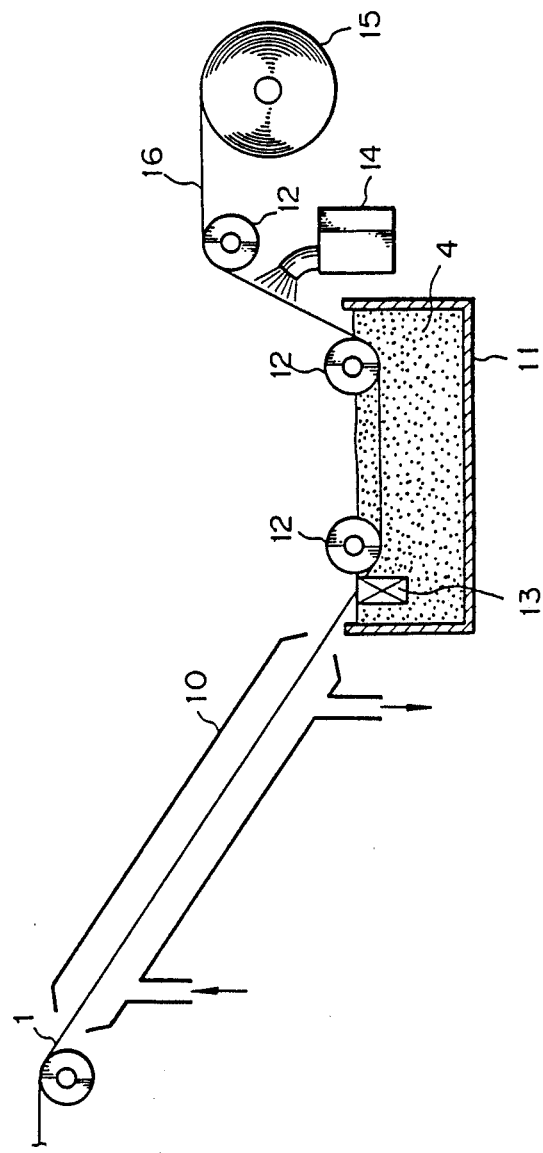

WATER-ABSORBING COMPOSITE BODY

TECHNICAL FIELD

The present invention relates to a water-absorbing composite body and a process for the preparation thereof. More particularly, the present invention relates to a water-absorbing composite body comprising a tape-shaped laminate having at least one layer of a high-melting-point synthetic resin and at least one layer of a low-melting-point synthetic resin, a split yarn obtained by splitting said tape-shaped laminate or a composite fibrous body having said laminate structure, and a powdery polymeric water absorber fusion-bonded to the surface thereof, and a process for the preparation of this water-absorbing composite body.

BACKGROUND ART

Waterproof covering materials formed by utilizing a water-absorbing or moisture-absorbing material are used in various fields. For example, in so-called conduction cables such as telecommunication cables and optical fiber communication cables, there must be no intrusion of water or moisture from the outside, and therefore, an especially elaborate waterproof covering is formed on the joins between cables. This waterproof covering is formed by applying a waterproof covering material to the join, winding a water-absorbing and moisture-absorbing material on the outer surface of the waterproof covering material, and coating a waterproof material such as a rubber on the water-absorbing and moisture-absorbing material. Water or moisture intruding into the covering layer through the outermost waterproof material is absorbed in the water-absorbing and moisture-absorbing material and is prevented from reaching the cable.

As the water-absorbing and moisture-absorbing material, there are used, for example, a split fiber of polyethylene glycol-impregnated polypropylene and a diethylene glycol-impregnated paper. However, these water-absorbing materials are difficult to handle because of their wettability, and furthermore, since a fluid is contained as the constituent, reproduction of the covering is very difficult.

As a means for solving these problems, a method has been proposed in which a powdery polymeric water absorber is incorporated and kneaded into a polyolefin at the extrusion step and a waterproofing property is imparted by subjecting the extrusion-shaped film to a drawing treatment and a splitting treatment. However, a polymeric water absorber generally has a poor resistance to heat, and if the polymeric water absorber is placed even at a melting temperature of a synthetic resin such as a polyolefin for a long time before extrusion shaping, the water-absorbing capacity is degraded, and moreover, the polymeric water absorber is substantially buried in the resin after extrusion shaping and the amount of the polymeric water absorber exposed to the surface is very small. Therefore, a satisfactory water-absorbing effect is not attained.

It is an object of the present invention to provide a water-absorbing material having a high water-absorbing efficiency and a good mechanical strength.

DISCLOSURE OF THE INVENTION

In accordance with one aspect of the present invention, there is provided a water-absorbing composite body comprising a tape-shaped laminate having at least one layer of a high-melting-point synthetic resin and at least one layer of a low-melting-point synthetic resin, in which at least a part of the low-melting-point synthetic resin layer is exposed to the surface, a split yarn obtained by splitting said tape-shaped laminate or a composite fibrous body having said laminate structure, and a powdery polymeric water absorber fusion-bonded to the outer surface of the low-melting-point synthetic resin layer exposed to the surface.

In accordance with another aspect of the present invention, there is provided a process for the preparation of a water-absorbing composite body, which comprises forming a tape-shaped laminate having at least one layer of a high-melting-point synthetic resin and at least one layer of a low-melting-point synthetic resin, in which at least a part of the low-melting-point synthetic resin layer is exposed to the surface, a split yarn by splitting said tape-shaped laminate or a composite fibrous body having said laminate structure; heating said laminate, split yarn or composite fibrous body at a temperature close to the melting point of the low-melting-point synthetic resin; and placing a powdery polymeric water absorber in contact with the heated tape-shaped laminate, split yarn or composite fibrous body, whereby the polymeric water absorber is fusionbonded to the outer surface of the low-melting-point synthetic resin layer exposed to the surface.

BRIEF DESCRIPTION OF THE DRAWINGS

FIG. 2 is a diagram illustrating the steps according to one embodiment of the process of the present invention; and, FIG. 3 is an enlarged sectional view illustrating a water-absorbing composite body on which a water-soluble resin film is wound according to the present invention.

BEST MODE FOR CARRYING OUT THE INVENTION

The base of the water-absorbing composite body of the present invention is a tape-shaped laminate having at least one layer of a high-melting-point synthetic resin and at least one layer of a low-melting-point synthetic resin, a split yarn obtained by splitting said tape-shaped laminate, or a composite fibrous body having said laminate structure.

As a tape-shaped laminate, there is used a tape obtained by drawing a laminate film comprising at least one layer of a high-melting-point synthetic resin and at least one layer of a low-melting-point synthetic resin, at least one surface of said laminate film being composed of the low-melting-point synthetic resin layer, and splitting the drawn film into a narrow width, or a tape obtained by splitting said laminate film and drawing the split film. Preferably, the thickness of the tape is 500 to 10,000 denier, especially 1,000 to 3,000 denier. The split yarn is formed by splitting the tape-shaped laminate (for example, by a splitting roll) into a net or a composite fiber. The single fiber width of the split yarn is preferably 0.03 to 0.2 mm, more preferably 0.03 to 0.11 mm, most preferably 0.03 to 0.07 mm.

Figure 1:
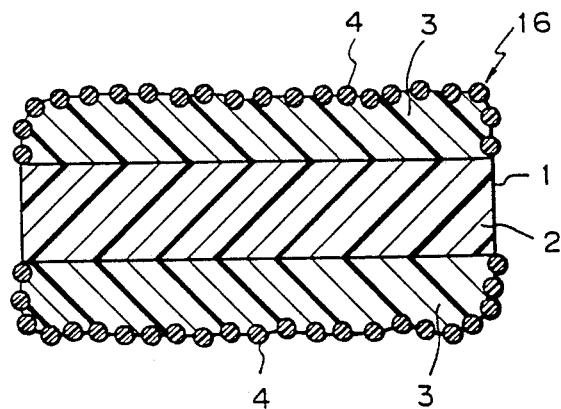
FIG. 1 is an enlarged sectional view illustrating the water-absorbing composite body of the present invention.

As preferred examples of the laminate film used for the preparation of the tape-shaped laminate or split yarn, there can be mentioned a two-layer laminate of high-melting-point synthetic resin layer/low-melting-point synthetic resin layer (referred to as "high/low two-layer laminate" hereinafter; other laminates will be similarly abbreviated), a low/high/low three-layer laminate (an example is shown in FIG. 1), and a low/ high- /low/high/low five-layer laminate.

As the composite fibrous body, there can be used a fibrous body obtained by drawing a side-by-side conjugate fiber comprising a high-melting-point synthetic resin component and a low-melting-point synthetic resin component, and a fibrous obtained by drawing a sheath-core conjugate fiber comprising a sheath of a low-melting-point synthetic resin and a core of a high-melting-point synthetic resin. Preferably, the fineness of the drawn conjugate fiber is 10 to 60 denier.

The number of layers in the tape-shaped laminate or the composite fibrous body is not particularly critical, but a laminate structure in which the high-melting-point synthetic resin forms an inner layer and the low-melting-point synthetic resin forms an outer layer is preferred. Preferably, the difference of the melting point between the high-melting-point synthetic resin and the low-melting-point synthetic resin is large, and a difference of at least 10° C. is generally preferred. Note, in the case of synthetic resins, where the melting point appears sharply, a small difference of the melting point is permissible.

In general, the high-melting-point synthetic resin is selected from thermoplastic synthetic resins such as isotactic polypropylene, high-density polyethylene, polyesters, nylon 6 and nylon 66.

A low-melting-point thermoplastic synthetic resin having a good bondability to the high-melting-point used. For example, there can be mentioned polyolefins such as low-density polyethylene, linear low-density polyethylene and high-density polyethylene; ethylene/ vinyl acetate copolymers; polyolefins such as lowdensity polyethylene, linear low-density polyethylene, high-density polyethylene and polypropylene, which are graft-modified with an unsaturated carboxylic acid or an anhydride thereof, such as maleic acid, fumaric acid, itaconic acid, maleic anhydride or itaconic anhydride (graft-modified high-density polyethylene and linear low-density polyethylene are preferred and a grafting ratio of 0.3 to 0.36% by weight is preferred), ethylene/ acrylate or methacrylate copolymers such as ethylene/ maleic anhydride/methyl methacrylate terpolymers, ethylene/acrylic acid copolymers and ethylene/ethyl acrylate copolymers; and thermoplastic resins partially neutralized with a metal such as sodium or zinc (that is, ionomer resins).

As preferred examples of the combination of the high-melting-point synthetic resin and the low-melting-point synthetic resin, there can be mentioned a combination modified linear low-density polyethylene, a combination of isotactic polypropylene and acid-graft-modified high-density polyethylene, a combination of isotactic polypropylene and an ethylene/maleic anhydride/methyl methacrylate terpolymer, ethylene/acrylic acid copolymer or ethylene/ethyl acrylate copolymer, and a combination of isotactic polypropylene and an ionomer resin.

A powdery polymeric water absorber is fushion-bonded to the outer surface of the low-melting-point synthetic resin layer exposed to the surface of the tape-shaped laminate, split yarn or composite fibrous body.

A powdery polymeric water absorber having a water absorption ratio of 500 to 1,000 is preferred. The water absorption ratio referred to herein is calculated by sufficiently dipping the powdery polymeric water absorber in water at normal temperature, removing excessive water by filtration using a screen (80 mesh), measuring the amount (weight) of absorbed water and dividing the amount of absorbed water by the weight of the water absorber before swelling. As preferred examples of the powdery polymeric water absorber having such a water absorption ratio, there can be mentioned crosslinked poly(sodium acrylate), a saponified acrylic acid/vinyl acetate copolymer and a starch/acrylic acid graft copolymer.

Preferably, the average particle size of the polymeric water absorber is so small that the low-melting-point synthetic resin layer exposed to the outer surface of the tape-shaped laminate, split yarn or composite fibrous body is covered as densely as possible. The average particle size is ordinarily 10 to 500 $\mu$m, preferably 10 to 300 $\mu$m, more preferably 10 to 50 $\mu$m, most preferably, 10 to 30 $\mu$m. If the average particle size exceeds 500 $\mu$m, the polymeric water absorber fails to form a dense covering and the surface condition of the composite body is degraded. Preparation and handling of a polymeric water absorber having an average particle size smaller than 10 $\mu$m are very difficult, and this polymeric water absorber is expensive.

Preferably, the amount of the fusion-bonded polymeric water absorber is 10 to 60% by weight based on the tape-shaped laminate, split yarn or composite fibrous body before fusion bonding.

In the water-absorbing composite body of the present invention, since the powdery polymeric water absorber is fusion-bonded to the surface, the waterabsorbing capacity based on the water absorber is very high. At the step of fusion-bonding the powdery polymeric water absorber, the low-melting-point synthetic resin layer is heated at a temperature close to the melting point thereof but the high-melting-point synthetic resin is little changed by heating, and therefore, the orientation state of the drawn tape-shaped laminate, split yarn or composite fibrous body is not lost and a good tensile strength is maintained.

The water-absorbing composite body of the present invention may be wound and enveloped with a tape of a water-soluble resin, if desired. When the waterabsorbing composite body of the present invention is wound with a tape of a water-soluble resin, falling of the powdery polymeric water absorber is prevented and a high water-absorbing capacity can be maintained. Moreover, the surface condition of the water-absorbing composite body is highly improved.

Figure 3:
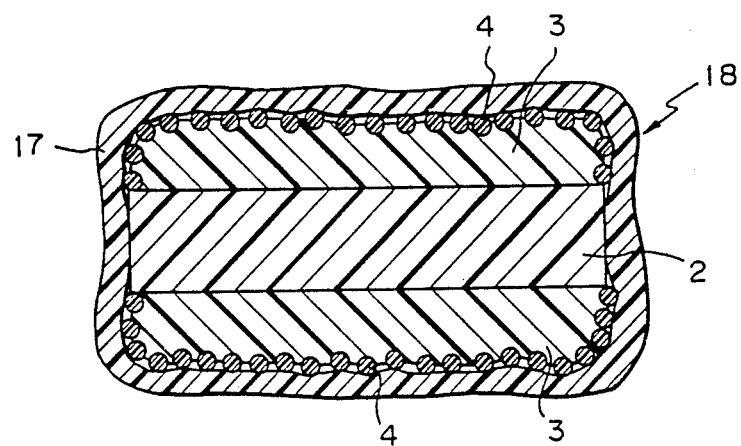

An example of the water-absorbing composite body not wound with a tape of a water-soluble resin is shown in FIG. 1, and an example of the water-absorbing composite body wound with a tape of a water-soluble resin is shown in FIG. 3. The water-absorbing composite body 16 shown in FIG. 1 has a structure in which a powdery polymeric water absorber 4 is fusion-bonded to both surfaces of a laminate tape comprising a low-meltingpoint synthetic resin layer 3, a high-melting-point synthetic resin layer 2, and a low-melting-point synthetic resin layer 3. The water-absorbing composite body 18 shown in FIG. 3 has a structure in which a water-soluble resin tape 17 is wound around the periphery of the water-absorbing composite body shown in FIG. 1.

When the water-soluble resin tape-wound waterabsorbing composite body is practically used, this tape is dissolved in water and the polymeric water absorber particles are exposed to exert a water-absorbing function. A polyvinyl alcohol tape is preferred as the water-soluble resin tape, and preferably, the thickness of the tape is 10 to 40 μm, more preferably 10 to 17 μm. In general, if the thickness of the water-soluble resin tape exceeds 40 μm, a time required for dissolution in water becomes necessary when the water-absorbing composite body is used, and the water-absorbing composite body is not preferably used in many fields. It is generally difficult to prepare a tape having a thickness smaller than 10 μm.

The process for the preparation of the water-absorbing composite body of the present invention will now be described.

The tape-shaped laminate can be obtained by forming a filmy laminate by co-extrusion of a high-melting-point resin and a low-melting-point resin or by lamination of a high-melting-point resin and a low-melting-point resin, and slitting the filmy laminate in a predetermined narrow width and drawing the slit laminate in the longitudinal direction or drawing the filmy laminate in the longitudinal direction and slitting the drawn laminate. Preferably, the thickness of the tape is 500 to 10,000 denier, especially about 1,000 to about 3,000 denier.

The split yarn can be obtained by splitting the above-mentioned tape-shaped laminate to a single yarn width of about 0.03 to about 0.2 mm by using, for example, a splitting roll. The split yarn can be used in the form of a bundle having a thickness of 500 to 10,000 denier, especially 1,000 to 3,000 denier. If the single yarn split width of the split yarn exceeds 0.2 mm, the amount of adhering polymeric water absorber is reduced and the touch of the water-absorbing composite body is degraded. It is difficult to split the tape into a split width smaller than 0.03 mm.

The composite fibrous body can be obtained by spinning a side-by-side conjugate fiber of a high-melting-point synthetic resin and a low-melting-point synthetic resin or a sheath-core conjugate fiber comprising a high-melting-point synthetic resin as the core and a low-melting-point synthetic resin as the sheath and drawing the conjugate fiber. Preferably, the fineness of the drawn composite fiber is 10 to 60 denier.

The steps of preparing the water-absorbing composite body according to one embodiment of the process of the present invention are illustrated in FIG. 2. Referring to FIG. 2, the tape-shaped laminate, split yarn or composite fibrous body 1 is heated almost to the melting point of the low-melting-point synthetic resin by a heating device 10 in which heated air is circulated. The tape-shaped laminate, split yarn or composite fibrous body, which is heated to such an extent that the surface of the low-melting-point synthetic resin layer is in the substantially molten state, is fed to a polymeric water absorber-applying device 11 and is passed through a polymeric water absorber 4 while being supported by a roll 12. At this point, the polymeric water absorber is fusion-bonded to the tape-shaped laminate, split yarn or composite fibrous body under an appropriate compressing force. Preferably, the powdery polymeric water absorber 4 is heated in advance at a temperature within the range whereat the water-absorbing effect is not lost (for example, 60° to 100° C.). In the case where this preheating is performed, when the polymeric water absorber comes into contact with the surface of the low-melting-point synthetic resin layer kept in the substantially molten state, rapid cooling of the molten surface is avoided and uniform fusion bonding can be attained. When the polymeric water absorber is applied to the split yarn, so that a large quantity of the polymeric water absorber can be uniformly fusion-bonded to the split yarn and the fusion-bonding effect can be further improved, preferably the width of the split yarn is expanded by a width-expanding device 13 and the split yarn passed through the path of the polymeric water absorber 4 in the width-expanded state. The tape-shaped laminate, split yarn or composite fibrous body 16, to which the polymeric water absorber 4 has been fusion-bonded, is then wound on a bobbin 15. Note, preferably, prior to winding, the tape-shaped laminate, split yarn or composite fibrous body 16 is passed through an atmosphere which is brought to a relative humidity of 60 to 90%, especially 75 to 85%, by a humidifier 14. In the humidifier 14 as shown in FIG. 2, it is sufficient if water is supplied in an amount of 0.1 to 0.5 l per hour. If this humidifying treatment is carried out, bonding of the powdery polymeric water absorber becomes complete and falling of the polymeric water absorber can be prevented. If the relative humidity exceeds 90%, a mutual bonding of split fibers occurs when the split yarn or the like is wound on the bobbin, and if the relative humidity is lower than 60%, a satisfactory effect can not be attained by the humidifying treatment.

Preferably, after fusion bonding of the polymeric water absorber but before the humidifying treatment, the split or the like is passed through a squeezing device (not shown) to remove any excess polymeric water absorber.

For fusion-bonding the polymeric water absorber to the low-melting-point synthetic resin layer, there may be adopted not only a method in which the split yarn or the like is passed through a vessel charged with the powdery polymeric water absorber, as shown in FIG. 2, but also a method in which the split yarn is passed through an atmosphere where the powdery polymeric water absorber is atomized and a method in which the powdery polymeric water absorber is scattered or sprayed to the split yarn or the like.

The water-soluble resin tape-wound water-absorbing composite body is prepared by winding a tape of a water-soluble resin on the periphery of the above-mentioned tape-shaped laminate, split yarn or composite fibrous body. As pointed out hereinbefore, preferably a tape of a water-soluble resin such as polyvinyl alcohol, and having a thickness of 10 to 40 μm, is used. If water is applied to the periphery by dipping, spraying or the like after winding of the water-soluble resin tape, the wound tape is well fitted to the waterabsorbing composite body and the shape is not lost, and the sealing by the tape is complete.

The present invention will now be described in detail with reference to the following examples.

Note, the water absorption ratio of the obtained water-absorbing composite body was determined by immersing 1 g of the water-absorbing fiber in 150 ml of distilled water at normal temperature for 5 minutes, pouring the swollen water-absorbing fiber on a net having a mesh size of 2 mm and a JK wiper, straining for 10 minutes, measuring the quantity of water flowing out, and calculating the water absorption ratio according to the following formula:

Water absorption ratio=150−(quantity of water flowing out)(ml)

Example 1

According to the following composition and recipe, a three-layer inflation film was formed, and the film was slit, drawn by a hot roll and split according to the procedures described below to obtain a split yarn.

Outermost Layer

Screw diameter: 40 mm;
Cylinder temperature $C_1$: 170° C.;
Cylinder temperature $C_2$: 230° C.;
Cylinder temperature $C_3$: 220° C.;
Low-density linear short-branch polyethylene (L-LDPE having a density Of 0.920, an MFR of 1.2 g/ 10 min, and a melting point of 120° C.) and melt-extruded.

Intermediate Layer

Screw diameter: 40 mm;
Cylinder temperature $C_1$: 180° C.;
Cylinder temperature $C_2$: 220° C.;
Cylinder temperature $C_3$: 230° C.;
Isotactic polypropylene (PP having a density of 0.90, an MFR of 3.0 g/10 min and a melting point of 160° C.) was melt-extruded.

Innermost Layer

Screw diameter: 32 mm;
Other conditions the same as for the outermost layer.
A three-layer inflation film comprising L-LDPE (10 μm)/PP (30 μm)/L-LDPE (10 μm) was taken up at a die lip of 1 mm and a take-up speed of 10.7 m/min, and the film was slit in a tape width of 8 mm and drawn at a draw roll temperature of 120° C. and a draw ratio of 5 in the longitudinal direction. The drawn film was split in a split width of 0.07 mm to obtain a split yarn having a thickness of 1,500 denier.

The obtained split yarn was treated by using the apparatus shown in FIG. 2 and a powdery polymeric water absorber was fusion-bonded thereto. More specifically, the split yarn 1 was first passed through the heating device 10 and the surface of the L-LDPE layer (low-melting-point resin layer) 3 was heated in the substantially molten state by air heated at 140° C. Then, this split yarn 1 was fed to the applying device 11 charged with the polymeric water absorber (saponified acrylic acid/vinyl acetate copolymer having a water absorption ratio of about 1,000) 4 having an average particle size of about 20 μm. The polymeric water absorber 4 was heated at a temperature of 70° to 80° C. by a known means, and the split yarn 1 was passed through the polymeric water absorber 4 while being supported by the roll 12. At this point, the adhering polymeric water absorber 4 was bonded to the split yarn 1 under an appropriate compression force, and since the bonded polymeric water absorber 4 per se was heated, the polymeric water absorber 4 was fusion-bonded to the surface of the low-melting-point resin layer 3 without lowering the surface temperature of the low-meltingpoint resin layer 3 in the substantially molten state, and even after the split yarn was fed out from the applying device 11, the polymeric water absorber 4 was tightly and densely bonded to the surface of the low-melting-point resin layer 3. Note, the width-expanding device 13 and humidifying device 14 were not used in the apparatus shown in FIG. 2.

The characteristic properties of the obtained water-absorbing composite body are shown in Table 1.

For comparison, a water-absorbing composite body was prepared in the same manner as described in Example 1 except that a split yarn composed solely of polypropylene and having a thickness of 1,500 denier was prepared and used and the polymeric water absorber was applied at a higher temperature (the temperature of the heated air was 160° C.). The results are shown in Table 1.

TABLE 1

| | Heating air Temperature (°C.) | Amount (%) of Applied Polymeric Water Absorber | Split Yarn after Application of Water Absorber | Water Absorption Ratio | Evaluation |
|---|---|---|---|---|---|
| Example 1 | 140 | 30 | Usable as split yarn | 60 | Good |
| Comparative Example 1 | 160 | 5 | Partially broken | 10 | Bad |

Example 2

A split yarn was prepared in the same manner as described in Example 1 except that LDPE (low-density polyethylene having a density of 0.921, an MFR of 0.4 g/10 min, and a melting point of 110° C.) was used as the low-melting-point synthetic resin instead of L-LDPE. A water-absorbing composite body was prepared from this split yarn in the same manner as described in Example 1 except that the heated air temperature was changed to 120° C. and the temperature of the polymeric water absorber was adjusted to 70° to 80° C.

In the obtained water-absorbing composite body, the amount of the fusion-bonded polymeric water absorber was and the polymeric water absorber was tightly and densely fusion-bonded and little falling was occurred. The water absorption ratio of the water-absorbing composite body was 70.

Examples 3 through 6

Polymeric water absorbers composed of crosslinked poly(sodium acrylate) (water absorption ratio of about having different average particle sizes, were applied and bonded to the split yarn obtained in Example 2, and with respect to each of the obtained waterabsorbing composite bodies, the amount of the applied polymeric water absorber and the water absorption ratio were determined. The results are shown in Table 2.

TABLE 2

| Example No. | Average Particle Size (μm) of Polymeric Water Absorber | Applied Amount (%) | Water Absorption Ratio |
|---|---|---|---|
| Example 3 | 10 | 45 | 70 |
| Example 4 | 20 | 35 | 60 |
| Example 5 | 30 | 20 | 40 |

Examples 7 through 10

The three-layer inflation film obtained in Example 2 was split in various widths by using splitting rolls having different needle intervals. In the same manner as described in Example 2, crosslinked poly(sodium acrylate) having an average particle size of about 20μm was fusion-bonded as the polymeric water absorber to the obtained split yarns and the polymeric water absorber-applied split yarns were treated at a relative humidity of 80% (the humidifier 14 was used). With respect to each of the obtained water-absorbing composite bodies, the amount of the applied polymeric water absorber and the water absorption ratio were measured. The results are shown in Table 3.

TABLE 3

| Example No. | Split Width (mm) of Split Yarn | Applied Amount (%) | Water Absorption Ratio |
| --- | --- | --- | --- |
| Example 7 | 0.03 | 50 | 110 |
| Example 8 | 0.05 | 40 | 90 |
| Example 9 | 0.07 | 30 | 80 |
| Example 10 | 0.3 | 10 | 50 |

Examples 11 and 12

Water-absorbing composite bodies were prepared in the same manner as described in Example 1 by using an HDPE-based (high-density polyethylene having a density of 0.950, an MFR of 1.2 g/10 min, and a melting point of 130° C.) ER resin or an L-LDPE-based (low-density linear polyethylene having a density of 0.920, an MFR of 4.0 g/10 min, and a melting point of 120° C.) ER resin, shown in Table 4, as the low-melting-point resin instead of LDPE and the same isotactic polypropylene as used in Example 1 as the high-melting-point resin, and the physical properties were measured. Note, crosslinked poly-(sodium acrylate) having an average particle size of 20 μm (water absorption ratio of about 600) was used as the polymeric water absorber, and the treatment was carried out at a relative humidity of 80% (the humidifier 14 was used) and a fusion-bonding speed of 10 m/min. The results are shown in Table 4.

TABLE 4

| Example No. | Low-Melting-Point Resin | MFR (g/10 min) | Density (g/cm³) | Applied Amount (%) | Water Absorption Ratio | Surface Condition after Application of Water Absorber |
| --- | --- | --- | --- | --- | --- | --- |
| Example 11 | ER resin* (HDPE-based) | 0.4 | 0.950 | 30 | 120 | Uniform and good |
| Example 12 | ER resin** (L-LDPE-based) | 3.5 | 0.920 | 30 | 120 | Uniform and good |

Note
*maleic anhydride grafting ratio = 0.33% by weight, melting point = 135° C.
**maleic anhydride grafting ratio = 0.35% by weight, melting point = 122° C.

As seen from the results shown in Table 4, the water-absorbing composite body obtained by using an ER resin has an excellent water absorption ratio and surface condition after application of the polymeric water absorber.

Examples 13 through 15

Water-absorbing composite bodies were prepared in the same manner as in Examples 3 through 6 except that the given relative humidity and the amount of crosslinked poly(sodium acrylate) (average particle size = 20 μm) applied as the polymeric water absorber were changed. The water absorption ratio and the bondability were examined. The results are shown in Table 5.

TABLE 5

| Example No. | Relative Humidity (%) | Applied Amount (%) | Water Absorption Ratio |
| --- | --- | --- | --- |
| Example 13 | 85 | 40 | 90 |
| Example 14 | 80 | 33 | 85 |
| Example 15 | 75 | 28 | 70 |

Each of the obtained water-absorbing composite bodies was wound on a bobbin for 10 hours and fed out from the bobbin, and the bondability was evaluated based on the condition at this point. In each of the water-absorbing composite bodies obtained in Examples 13, 14 and 15, a good bonding was maintained between the polymeric water absorber and the split yarn, each water-absorbing composite body could be smoothly taken out from the bobbin, and the surface condition was good.

Example 16

The three-layer inflation film (10 μm L-LDPE/30 μm PP/10 μm L-LDPE) obtained in Example 1 was slit into a tape having a width of 8 mm and the tape was drawn at a drawing roll temperature of 120° C. and a draw ratio of 5 in the longitudinal direction to obtain a tape having a thickness of 1,500 denier. The obtained tape was treated in the same manner as the split yarn was treated in Example 1, whereby the powdery polymeric water absorber was fusion-bonded to the tape. Note, cross-linked poly(sodium acrylate) (having a water absorption ratio of about 600) having a particle size of 20 μm was used as the polymeric water absorber. In the obtained tape-shaped water-absorbing composite body, the amount of the fusion-bonded polymeric water absorber was 40% and the water absorption ratio was 80, and the surface condition was good.

Example 17

According to the composition and recipe shown below, a side-by-side two-layer conjugate fiber was spun.

Side 1

Screw diameter: 40 mm;
Cylinder temperature $C_1$: 170° C.;
Cylinder temperature $C_2$: 240° C.;
Cylinder temperature $C_3$: 230° C.;
Low-density linear short-branch polyethylene (L-LDPE) having a density of 0.920, MFR of 9.0 g/10 min and a melting point of 120° C.

Side 2

Screw diameter: 40 mm;
Cylinder temperature $C_1$: 180° C.;
Cylinder temperature $C_2$: 220° C.;
Cylinder temperature $C_3$: 250° C.;

Isotactic polypropylene (PP) having a density of 0.90, MFR of 15.0 g/10 min and a melting point of 160° C.

L-LDPE and PP were conjugate-spun at a draft ratio of 100 from nozzles having a hole diameter of 1.0 mm. The spun fiber was drawn at a drawing roll temperature of 130° C. and a draw ratio of 2 to obtain a conjugate fiber having a fineness of 20 denier.

By using the apparatus shown in FIG. 2, the obtained conjugate fiber was treated in the same manner as the split yarn was treated in Example 1, whereby the powdery polymeric water absorber was fusion-bonded to the conjugate fiber. Note, crosslinked poly(sodium acrylate) (having a water absorption ratio of about 600) having an average particle size of 10 μm was used as the powdery polymeric water absorber and this polymeric water absorber was applied after pre-heating at about 80° C.

In the obtained water-absorbing composite body, the amount of the fusion-bonded polymeric water absorber was 15%, the water absorption ratio was 25, and the surface condition was good.

Example 18

A three-layer film (10 μm L-LDPE/30 μm PP/10 μm L-LDPE) was prepared in the same manner as described in Example 1 except that the T-die method was adopted instead of the inflation method. The film was drawn in the same manner as described in Example 1 to obtain a split yarn having a fineness of 1,500 denier.

By using the apparatus shown in FIG. 2, a powdery saponified acrylic acid/vinyl acetate copolymer was fusion-bonded to the obtained split yarn according to the same method as described in Example 1. Note, the split yarn was guided to the polymeric water absorber-applying device 11 while the width was being expanded by the width-expanding device 13, and the split yarn coming out from the applying device 11 was passed through an atmosphere brought to a relative humidity of 80% by the humidifying device 14. In the obtained water-absorbing composite body, the amount of the fusion-bonded polymeric water absorber was 50%.

A polyvinyl alcohol film having a thickness of about 15 μm was slit to a tape having a width of 15 mm, and the tape was wound around the above-mentioned water-absorbing composite body. Then, the tape-wound composite body was immersed in water at normal temperature for about 2 seconds and dried at 120° C. for 2 minutes. Thus, a water-absorbing composite body having a section as shown in FIG. 3 and a thickness of 9,400 denier was obtained. The water absorption ratio of the water-absorbing composite body was 50, and no falling of the polymeric water absorber was observed.

INDUSTRIAL APPLICABILITY

Since the water-absorbing composite body of the present invention has a high water absorption efficiency and retains a good mechanical strength, the waterabsorbing composite body of the present invention can be widely used as a water-absorbing material in various fields. Namely, the water-absorbing composite body of the present invention is valuable as a waterproof covering for a conduction cable such as a telecommunication cable or an optical fiber communication cable, a sanitary article such as a sanitary napkin or a disposable diaper, a dewing-preventing sheet, an agricultural or horticultural water-retaining sheet, a ribbon-shaped water-absorbing material and the like.

What is claimed is:

1. A water-absorbing composite body comprising (A) a split yarn obtained by splitting a tape-shaped three-layer laminate composed of a low-melting point synthetic resin layer, a high-melting point synthetic resin layer, and a low-melting point synthetic resin layer, wherein the two low-melting point synthetic resin layers are exposed on the surface of the laminate, and B) a powdery polymeric water-absorber fusion-bonded to the exposed surface of each low-melting point synthetic resin layer.

2. A water-absorbing composite body as set forth in claim 1, wherein the high-melting-point synthetic resin is selected from the group consisting of isotactic polypropylene, high-density polyethylene, a polyester, nylon 6, and nylon 66.

3. A water-absorbing composite body as set forth in claim 1, wherein the low-melting-point synthetic resin is selected from the group consisting of low-density polyethylene, linear low-density polyethylene, high-density polyethylene, an ethylene/vinyl acetate copolymer, a polyolefin graft-modified with an unsaturated carboxylic acid or an anhydride thereof, an ethylene/maleic anhydride/methyl methacrylate terpolymer, an ethylene/acrylic acid copolymer, an ethylene/ethyl acrylate copolymer and an ionomer resin.

4. A water-absorbing composite body as set forth in claim 1, wherein the difference of the melting point between the high-melting-point synthetic resin and the low-melting-point synthetic resin is at least 10° C.

5. A water-absorbing composite body as set forth in claim 1, wherein the split yarn has a thickness of 500 to 10,000 denier.

6. A water-absorbing composite body as set forth in claim 1, wherein the split yarn has a split width of 0.03 to 0.2 mm.

7. A water-absorbing composite body as set forth in claim 1, wherein the powdery polymeric water absorber has a water absorption ratio of 500 to 1,000.

8. A water-absorbing composite body as set forth in claim 1, wherein the powdery polymeric water absorber is selected from the group consisting of crosslinked poly(sodium acrylate), a saponified acrylic acid/vinyl acetate copolymer, a starch/acrylic acid graft copolymer and an isobutylene/maleic anhydride copolymer.

9. A water-absorbing composite body as set forth in claim 1, wherein the average particle size of the powdery polymeric water absorber is 10 to 500 μm.

10. A water-absorbing composite body as set forth in claim 1, wherein the average particle size of the powdery polymeric water absorber is 10 to 300 μm.

11. A water-absorbing composite body as set forth in claim 1, wherein the average particle size of the powdery polymeric water absorber is 10 to 50 μm.

12. A water-absorbing composite body as set forth in claim 1, wherein the average particle size of the powdery polymeric water absorber is 10 to 30 μm.

13. A water-absorbing composite body as set foerth in claim 1, wherein the amount of the fusion-bonded powdery polymeric water absorber is 10 to 60% by weight based on the split yarn before the fusion bonding.

14. A water-absorbing composite body as set forth in claim 1, wherein the split yarn, to which the powdery polymeric water absorber is fusion-bonded, is wound and enclosed with a tape of a water-soluble resin.

15. A water-absorbing composite body as set forth in claim 14, wherein the water-soluble resin is polyvinyl alcohol.

* * * * *